(12) United States Patent
Andreussi

(10) Patent No.: US 8,730,461 B2
(45) Date of Patent: May 20, 2014

(54) METHOD FOR MONITORING FUGITIVE GAS EMISSIONS FROM THE SOIL, VIA VERTICAL CONCENTRATION MEASUREMENTS

(75) Inventor: Paolo Andreussi, Pisa (IT)

(73) Assignee: Tea Sistemi S.p.A., Pisa (IT)

( * ) Notice: Subject to any disclaimer, the term of this patent is extended or adjusted under 35 U.S.C. 154(b) by 0 days.

(21) Appl. No.: 13/823,296

(22) PCT Filed: Oct. 4, 2011

(86) PCT No.: PCT/IB2011/054351
§ 371 (c)(1),
(2), (4) Date: Apr. 22, 2013

(87) PCT Pub. No.: WO2012/046180
PCT Pub. Date: Apr. 12, 2012

(65) Prior Publication Data
US 2013/0208262 A1 Aug. 15, 2013

(30) Foreign Application Priority Data
Oct. 6, 2010 (IT) ................................ FI2010A0208

(51) Int. Cl.
*G01N 21/00* (2006.01)

(52) U.S. Cl.
USPC .......................................................... 356/72

(58) Field of Classification Search
USPC .......................................... 356/72, 51; 702/2
See application file for complete search history.

(56) References Cited

U.S. PATENT DOCUMENTS

| | | |
|---|---|---|
| 4,135,092 A | 1/1979 | Milly |
| 6,542,242 B1 | 4/2003 | Yost et al. |

(Continued)

FOREIGN PATENT DOCUMENTS

WO WO 2009/156437 A2 12/2009

OTHER PUBLICATIONS

K.P. Heue et al Direct Observation of Two Dimensional Trace Gas Distributions With an Airborne Imaging DOAS Instrument; Atmospheric Chemistry and Physics; 2008; pp. 6707-6717.

(Continued)

*Primary Examiner* — Tarifur Chowdhury
*Assistant Examiner* — Jamil Ahmed
(74) *Attorney, Agent, or Firm* — Lucas & Mercanti, LLP

(57) ABSTRACT

Method for the quantification of the fugitive gas flow from a dispersed source (A) by monitoring with a remote detection optical instrument mounted on an aircraft (UAV) which moves at a determined height along a plane (S) perpendicular to the direction of the wind field (u), such wind field being known through suitable positioning of meteorological stations within and in areas neighboring the site to be monitored according to known techniques and use of commercially available diagnostic meteorological models. By this instrument discrete vertical measurements are carried out of the fugitive gas concentration averaged over said height along the whole width (W) of the plane (S) to yield corresponding mean vertical concentration values and, according to mean wind speed values detected at said discrete vertical measurements, a value of the fugitive gas flow (Q) is obtained by integrating the product of the mean vertical concentration values and of the corresponding mean wind speed values with respect to the surface of the sampling plane (S). The obtained value of the fugitive gas flow (Q) is corrected by a corrective factor (a) obtainable by comparing concentration values obtained by direct measurements and values calculated by dispersion models.

6 Claims, 3 Drawing Sheets

(56) References Cited

U.S. PATENT DOCUMENTS

| | | |
|---|---|---|
| 6,864,983 B2 | 3/2005 | Galle et al. |
| 6,895,335 B2 * | 5/2005 | Archibald et al. ............ 702/2 |
| 7,075,653 B1 | 7/2006 | Rutherford |
| 7,312,452 B2 | 12/2007 | Klingenberg et al. |
| 7,486,399 B1 | 2/2009 | Reichardt et al. |
| 7,508,520 B1 | 3/2009 | Lines et al. |
| 7,523,638 B2 | 4/2009 | Prince |
| 2010/0091267 A1 * | 4/2010 | Wong ............................ 356/51 |
| 2010/0131207 A1 | 5/2010 | Lippert et al. |

OTHER PUBLICATIONS

S. Broccardo et al; Airborne Imaging Differential Optical Absorption Spectroscopy; Trace-Gas Measuremenets Fro the Suburbs to the Sub-Continent; 2009 IEEE; pp. 1044-1047.

\* cited by examiner

METHOD FOR MONITORING FUGITIVE GAS EMISSIONS FROM THE SOIL, VIA VERTICAL CONCENTRATION MEASUREMENTS

CROSS-REFERENCE TO RELATED APPLICATION

This application is a 371 of PCT/IB2011/054351, filed Oct. 4, 2011, which in turn claims the benefit of priority from Italian Patent Application Serial No. FI2010A000208, filed Oct. 6, 2010, the contents of each of which are incorporated herein by reference.

FIELD OF THE INVENTION

The present invention refers to the field of the detection and control of sources of atmospheric pollution and more precisely it regards the mapping of gaseous emissions especially by using unmanned aerial vehicles, (UAVs), by using remote detection techniques. More in particular the invention refers to a method for the detection of emissions from the soil of potentially hazardous gaseous substances dispersed in the air such as, but not limited to, methane or carbon dioxide, in terms of total gas flow emitted and characterization and localisation of the source of emission. The present invention is particularly, but not exclusively, suitable for monitoring sites such as gas pipelines, waste sites, industrial plants, animal rearing farms and natural sources, for the possible detection of the gas flow emitted from area or point sources placed on the ground, even when it is not known where the emissions source is on the site to be monitored.

STATE OF THE ART

The detection of atmospheric gaseous pollutants and contaminants was extensively studied both for stationary and mobile applications.

The traditional instruments for the monitoring the pollutant substances dispersed in the air consist of accurate detection systems based on spectrophotometric cells, catalytic or electrochemical sensors. The latter represent developed technologies available on the market in which the detection is not remote, i.e. it operates by sampling the gas within the instrument.

Two recent application examples of such technology are described in U.S. Pat. Nos. 6,864,983 and 7,523,638. The first of these patents describes a method for measuring emissions or gaseous flows by using a spectrophotometric instrument. The second of the aforementioned patents allows localising the gaseous source and the quantification of the gaseous flows through a spatial and temporal verification of the gas concentrations. However, though rigorous, even at very low ranges of concentrations, these measurements apply in an extremely effective manner to small sites and, given the accurateness of the measurement, they may have limitations for applications to vast areas.

Particularly important in the field of atmospheric monitoring are remote optical monitoring techniques (ROMT) which apply "open path" measurement systems based on the measurement of the selective absorbance of the radiation on a given optical path tens or hundreds of meters long.

A stationary optical system for the simultaneous mapping of more gaseous contaminants in the air using these technologies is described in the U.S. Pat. No. 6,542,242. The method described in this patent is based on the spatial mapping of the concentrations of fugitive gases through measurements using path integrated—optical remote sensing (Pi-ORS) methods such as DIAL (Differential Absorption LIDAR) or FTIR (Fourier Transform Infra-Red). A cumulative distribution function is used to create the mapping of the contaminants which may include the localization of the source of contamination. Spatial distribution maps are produced by using a plurality of non-superimposed luminous beams, which radially depart from a common origin on the sampling area both in the horizontal and vertical direction. In addition this system requires the use of back-reflectors on the axes of the beams along which the energy is emitted, the positioning of such back-reflectors being quite expensive and difficult on vast surfaces. Furthermore the mapping thus obtained solely regards the concentrations of pollutants, without considering the meteorological conditions present in the area of interest and does not give any indication regarding the flows.

A method for mapping natural gas both for stationary and portable applications is described in the U.S. Pat. No. 7,486,399. The system measures the backscattered light by scanning limited portions of areas for the reconstruction of images which, in real time, reveal the presence of methane by means of remote measurements. Though providing the mapping in terms of concentration of natural gas in the area of interest in real time, the method disclosed in the aforementioned patent is not capable of providing the actual localization of the source of emission because it does not consider the wind fields present in the area.

Heue et al (2008) and Broccardo and Piketh (2009) use instruments for the remote detection by optical means based on the differential optical absorption spectroscopy (DOAS). These instruments are suitably installed on an aircraft flying at high altitude (approx, 4500 m asl) so as to produce bidimensional mapping of trace gases on planes perpendicular to the flight direction. The proposed technique is developed for the detection of trace gases emitted at high altitude (for instance gases coming from chimneys and/or volcanoes). These mappings are not necessarily based on the knowledge of the position of the emission sources in the site, but anyway they are carried out mostly directly above the sources (and not in such a way that the site has to be entirely fathomed). In this way the sources that are downwind with respect to the flight path are not detected, as it is evident for at least one of the cases considered by Heue at al. (2008), if a complete mapping of the entire site is not carried out. Furthermore, the Broccardo and Piketh (2009) method accomplishes a continuous scan of the whole site according to paths that are in general curvilinear, and implies that a variable angle is formed between the flight direction and the wind direction, as the aircraft moves. The flow value is calculated by taking into account this angle. When applied to the detection of fugitive gases emitted at height, this method allows to calculate the flow by disregarding the variation of the wind as the flight height increases, that on the contrary should be considered for the characterization of the sources on the ground (for instance emissions from pipelines or landfills). In view of what said above, this method is onerous when applied to multiple emission sources not localised on the site to be monitored because for a correct evaluation of the trace gas flow on the site under monitoring, the measurement should be carried out by fathoming the whole site so that all sources are identified and quantified.

A technique of inversion of the dispersion models is used for the localisation of the emission source according to U.S. Pat. No. 6,895,335. This patent is based on the comparison between concentration data obtained by horizontal measurements with point detection sensors and data calculated by using the dispersion method for each of the hypothesised emission sources, assuming for each of them position and flow and taking into account the wind speed. In particular, the dispersion model used is that of the classical theory that correlates the concentration values starting from the source flow and position. Among the hypothesised sources, it is taken the source providing the concentration values calculated by the dispersion model that are closer to the values measured. Obviously, the thicker is the web of analysed combinations, even if detrimental to the rapidity of calculation, the more accurate is the method.

The patent application No. WO 2009/156437 A2 in particular utilises the above said technique of inverted dispersion by using, for the data acquisition, a mobile platform on which a point detection sensor is mounted for horizontal measurement of concentration. The data acquisition is accomplished by scanning the whole site from above, preferably in direction perpendicular to the wind direction.

The methodology of inversion of the dispersion models allows to identify and quantify the source flow in the site, but it is onerous in terms of required scans, especially for relatively wide sites, besides being a little accurate and requiring a huge computational effort.

Portable systems that apply remote optical detection methods of the absorption DIAL type are described in U.S. Pat. No. 7,508,520 and No. 7,312,452. In the first of these patents a mobile system is described having a compact and stable structure, for the detection of accumulations of methane, which can be assembled on helicopters in particular. In the second patent described are a method and a system for the detection and simultaneous mapping of several fluids by using an aircraft for monitoring traces of fluids leaking from pipes traversing the subsoil up to the atmosphere. Regardless of the high degree of sensitivity of the instruments used, the aforementioned systems are limited to measuring the concentration data without considering the meteorological data: furthermore the use of such instruments, in combination with aerial means, requires quite high investment and management costs.

The U.S. Pat. No. 4,135,092 describes a method for the quantification of the flows of fugitive emissions by using aircraft and taking into account the wind field. For the quantification of the mass flow of a gaseous effluent that exits from a distributed source there is defined a sampling plane which is downwind and perpendicular to the wind direction. Concentration measurements of the gaseous pollutant streams in the horizontal direction against back-reflectors mounted at various heights on a vertical support suspended on an aircraft (airplane or helicopter) are carried out on such plane. Requiring the use of aircrafts, this invention reveals the drawback of being quite expensive and the use of back-reflectors makes the use of the apparatus difficult to manage.

Lastly a method and relative apparatus for the detection of gas, such as methane, based on the open path optical detection technology called TDLAS (Tunable Diode Laser Absorption Spectroscopy), which exploits the spectroscopic absorption combined with the use of an advanced diode laser, is described in U.S. Pat. No. 7,075,653. This apparatus uses—for the detection of the fugitive gas—a light beam emitted by a laser with a wavelength generally corresponding to the absorption band of the gas, and illuminates a target. A portion of the received light beam is reflected by the target to the detector and analysed thus detecting a mean concentration of the gas on the length that the light beam has travelled. Such instrument, not requiring the use of back-reflectors, is manageable, reliable and sensitive also at low levels of detected gas concentration.

SUMMARY OF THE INVENTION

Subject of the present invention is to provide a method for monitoring a possible leakage of a gas such as, for example, methane or $CO_2$, particularly from area sources that is reliable and simultaneously simple to carry out.

A particular subject of the present invention is to provide a method of the aforementioned type that, even without knowing the position of the possible emission source in the site to be monitored, allows the quantification of the fugitive gas flow with a relatively limited number of scans.

Another subject of the present invention is to provide a method of the aforementioned type also capable of allowing the identification of the source of pollutant gas.

The method according to the invention, through remote concentration measurements using optical methods, in combination with meteorological models, allows quantifying the total gas flow emitted, as well as a mapping of the flow, also allowing the localisation, the extent of the fugitive gas flow and, in the case of non-uniform flows, the characterisation of the fugitive emissions in terms of discrete quantification of the contributions to the total flow. The mapping thus proposed allows within practical times the definition of suitable safety measures to be adopted and interventions suitable for confining and/or interrupting the emission of the fugitive gas from the soil.

According to an important aspect of the present invention the proposed method, providing concentration measurements with remote detection optical instruments which do not require the use of back-reflectors has the advantage of also easily monitoring sites of irregular orography, with a high degree of accuracy and low costs. Furthermore, using an optical detection technology such as TDLAS, it allows attaining the further advantage of not requiring calibrating the measurements in advance. The specific use of aircrafts allows the environmental monitoring and protection also in remote sites—hazardous and inaccessible using other means—and the use of the UAV specifically presents the further advantage of avoiding involving personnel potentially exposed to health risks.

According to another important aspect of the invention the proposed method provides for an estimation of the direction and speed of the wind by using diagnostic meteorological models available on the market, such as for example CAL-MET (CALifornian METereological model) for the evaluation of the wind direction and speed. Forecasting the accurate evolution of the three-dimensional wind field in the area neighbouring the involved area (Near Field), requires the installation of meteorological stations placed in strategic points of the field to be monitored according to techniques of the known art.

The main methodological element of the present invention provides for the vertical concentration measurements, averaged on the flight height H, downwind and in direction—at least in first approximation—perpendicular to the wind direction.

In particular the methodology provides for the definition of an ideal plane arranged downwind and perpendicular thereto, having a width sufficient to contain the projection of the site to be monitored and placed at a distance from the site such to contain, at the aircraft sampling height, the whole gaseous effluent released from the site. The aircraft, bearing the remote detection optical instrument, overflying the site to be mapped at a height within the aforementioned ideal plane, provides discrete vertical measurements of fugitive gas concentration mediated on the height. According to such measurements the pollutant flow can be evaluated. The method according to the invention has the advantage to allow the identification and quantification of the fugitive gases flows in relatively wide sites (of the order of thousands of square meters) with a limited number of concentration measurements.

BRIEF DESCRIPTION OF THE DRAWINGS

Further characteristics and advantages of the method for the quantification of the fugitive gas flow according to the present invention will be easier to understand from the following description of an embodiment thereof, provided by way of non-limiting example, with reference to the attached drawings wherein.

DETAILED DESCRIPTION OF THE INVENTION

Figure 1:
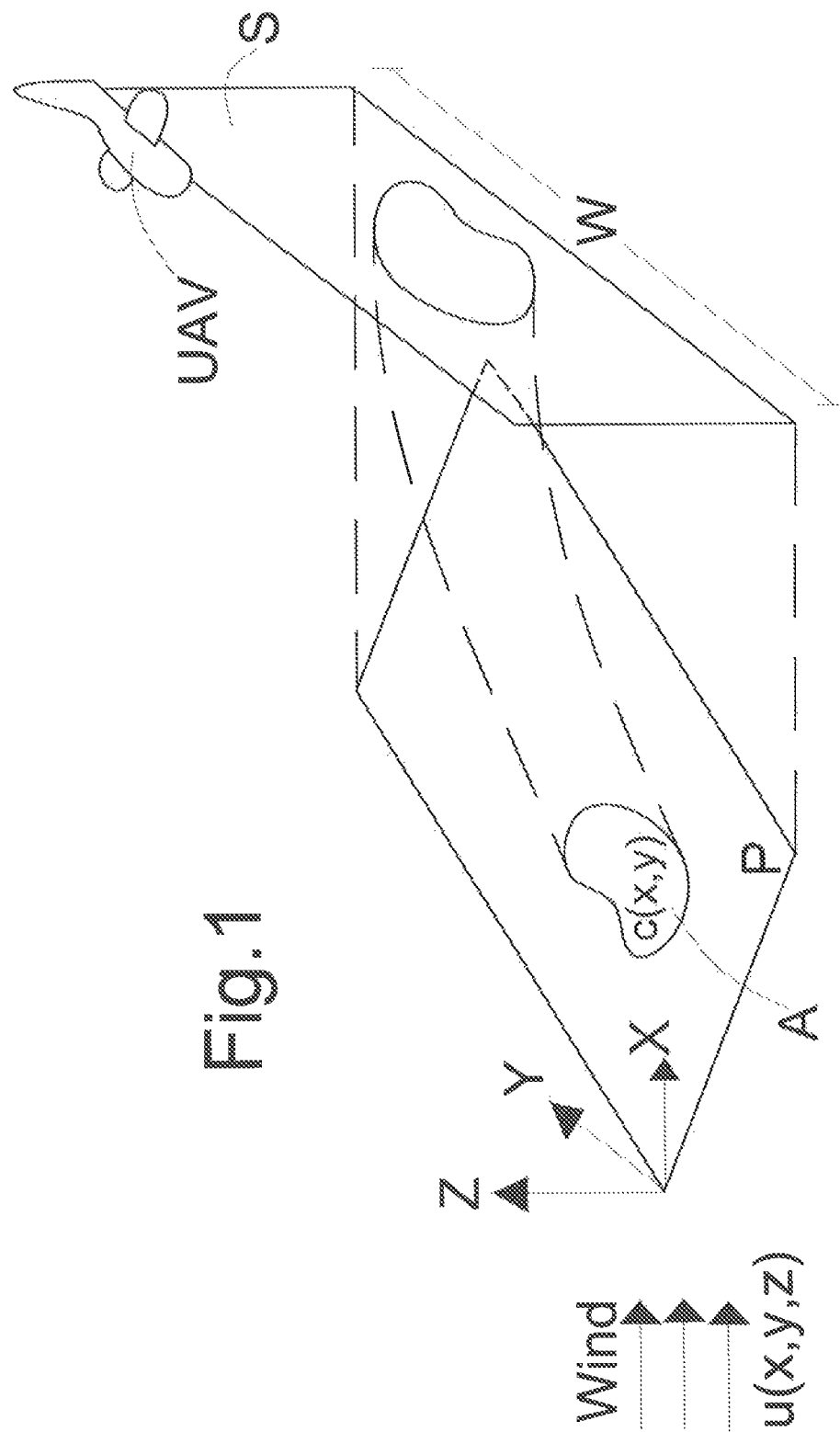
FIG. 1 schematically shows an aircraft for the vertical sampling of concentrations of fugitive emissions, along a sampling plane arranged downwind with respect to the site containing the source of dispersion.

With reference to FIG. 1, the site of a generic dispersed source, assimilated to a plane surface of coordinates (x,y) is indicated with P. Assuming the point flow q(x,y) constant during the measurement and indicated with A the area corresponding to the extent of the source of fugitive gas, said area being contained in the site to be monitored P, the total fugitive gas flow is described by the following equation:

$$Q = \int_A q(x_0, y) \, dA \quad (1)$$

The equation (1) in the case of uniform area source $q_0$ in the area A is simplified as follows:

$$Q = q_n A \quad (2)$$

The wind direction is that of the axis x and $x_0$ is the distance at which a vertical sampling plane S is pieced with respect to the point of the site P impacted—as the first—by the wind. The sampling plane S has a width W such as to contain the projection of the site to be monitored P. Once the generic wind field is indicated with u(x,y,z), the wind field present on S is indicated with u($x_0$,y,z). Using meteorological stations placed in nearby areas and within the site to be monitored for the detection of meteorological data, using diagnostic meteorological models (for example, CALMET, Californian Meteorological Model), the wind field present on site P, and in particular at the plane S, may be obtained. As the point concentration of the fugitive gas on the plane S is indicated with c($x_0$,y,z), the total fugitive gas flow emitted can be assimilated to the sole convective flow and described by the following expression:

$$Q = \int_S u(x_0, y, z) c(x_0, y, z) \, dS = \int_V \left\{ \int_H u(x_0, y, z) c(x_0, y, z) \, dz \right\} dy \quad (3)$$

Figure 2:
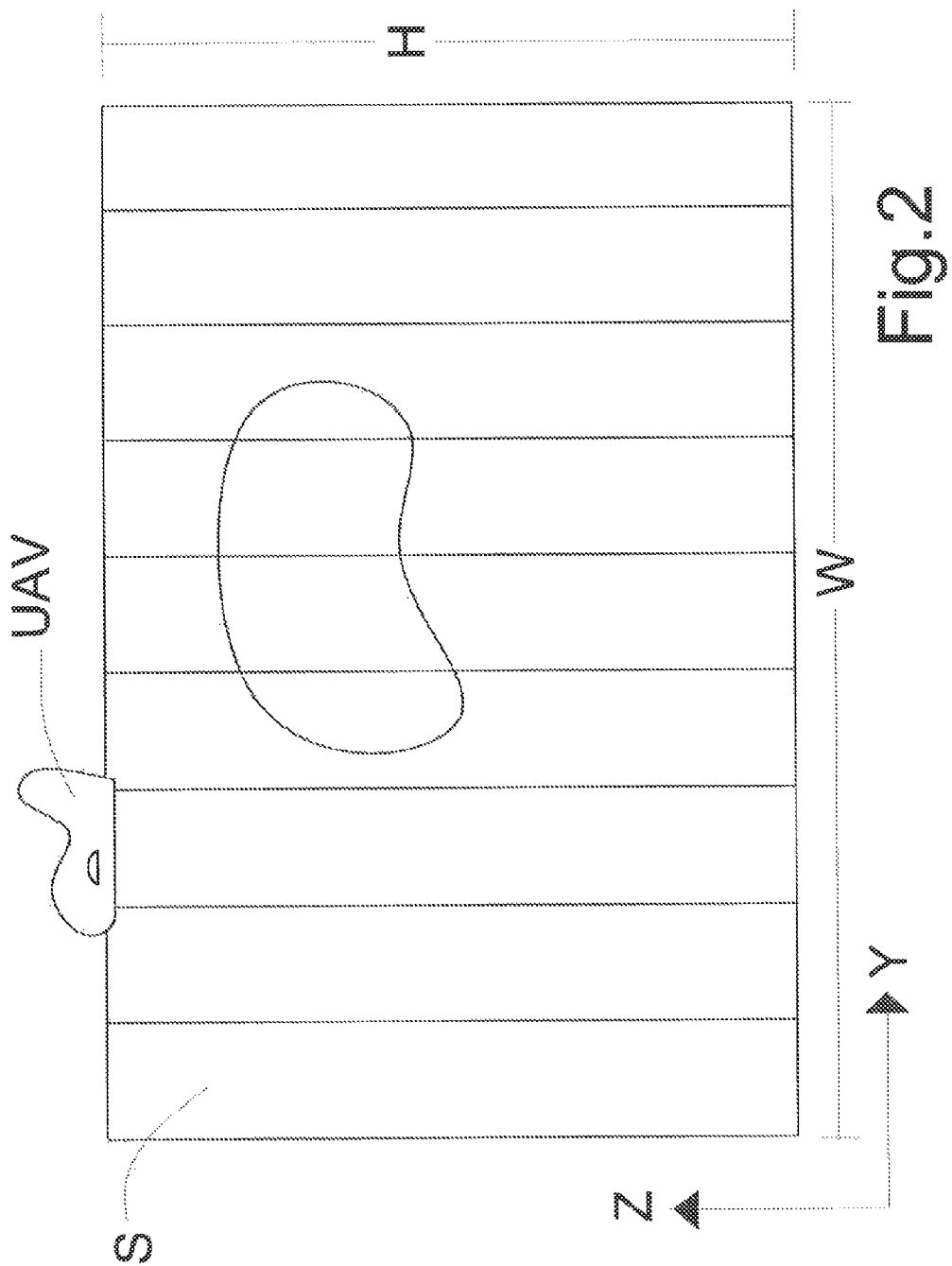
FIG. 2 shows the cloud of fugitive gas on the sampling plane of FIG. 1 and the relative grid of vertical concentration measurements on the same plane.

With reference to FIG. 2, using a remote detection optical instrument (for example, TDLAS) mounted on the lower part of an aircraft UAV which moves along the plane S at the height H such that the cloud of fugitive gas remains below said height, at the generic coordinate y there is measured the mean vertical concentration value $\bar{c}_H(x_0,y)$, knowing the corresponding mean speed value of the wind $\bar{u}(x_0,y)$. The flow value can be rewritten multiplied by an empirical coefficient $\alpha$ as indicated below:

$$Q = \alpha H \int_0^W \bar{u}(x_0, y) \cdot \bar{c}_H(x_0, y) \, dy \quad (4)$$

wherein $\bar{u}(x_0,y)$ is the wind speed averaged on the vertical coordinate in position ($x_0$,y).

The equation (4) allows the quantification of the flow starting from experimental measurements along the vertical plane of sampling S of average concentrations on the height H ($\bar{c}_H$), detected by the optical instrument of detection and wind average speed ($\bar{u}$), when the coefficient $\alpha$ is assessed, this coefficient being defined by comparing the equations (3) and (4) according to the equation (5):

$$\alpha = \frac{\int_W \left( \int_H u(x_0, y, z) c(x_0, y, z) \, dz \right) dy}{H \int_0^W \bar{u}(x_0, y) \cdot \bar{c}_H(x_0, y) \, dy} \quad (5)$$

The coefficient $\alpha$ is assessed by using mathematical methods of dispersion, such as Gaussian models or more advanced models available on the market (for instance CALPUFF), in which the point variables (c($x_0$,y,z) and u($x_0$,y,z)) and the average variables ($\bar{c}_H$, $\bar{u}$) are calculated as solution of the dispersion model. The plume may be described and the point and average concentration values may be calculated as function of the class of stability of the wind, by using the dispersion model on study cases, where the position and flow of the source are assigned, as well as the site extent, the orography of the territory and the vegetation coverage.

For the characterisation of the sources on the ground the proposed method requires the calculation of the vertical gradients of speed and concentration (due to the limit layer on the ground).

The dependency of the flow from these gradients, calculated according to Equation (4) starting from experimental measurements of concentration and speed averaged along the height H, is contained in the coefficient $\alpha$, that characterised therefore the proposed methodology from that of Broccardo and Piketh (2009), where sources at high altitude are considered and therefore vertical gradients for the speed and concentration are taken as null.

From the comparison the corrective coefficient $\alpha$ depends mainly on the intensity and class of stability of the wind, whereas the effect of the distance of the source on such coefficient is minor. According to the methodology of the present invention, the concentration is detected on a plane outside the site, placed at a distance from the source sufficient to contain the whole plume (of the order of some tens of meters). For distances of detection of the same order of or higher than those hypothesised, the influence of the position of the emission source on the corrective coefficient $\alpha$ is almost negligible.

On the basis of the hypotheses proposed, the corrective coefficient $\alpha$ for the flow calculation according to the Equation (4) may be calculated a priori, disregarding the effect of the position of the source inside the site, based on the characteristics of any sites (orography, vegetation coverage) and as function of the class of stability and of the wind speed.

As an example, in Table 1 are reported the values of the corrective coefficient α for a flat site, void of shrubs, as function of the class of stability and of the wind speed. As highlighted in Table 1, the values calculated for the corrective coefficient α increase with the wind instability and slightly vary with the wind speed.

TABLE 1

Example of values taken by the corrective coefficient α as function of the class of stability and speed of the wind for a flat site, void of vegetation

| | Corrective coefficient α | | | | |
|---|---|---|---|---|---|
| v(m/s) | Classe A | Classe B | Classe C | Classe D | Classe F |
| 0.5 | 0.86 | 0.77 | 0.74 | 0.69 | 0.49 |
| 1 | 0.87 | 0.78 | 0.74 | 0.69 | 0.49 |
| 2 | 0.91 | 0.81 | 0.75 | 0.69 | 0.49 |
| 3 | 0.90 | 0.81 | 0.75 | 0.69 | 0.49 |
| 4 | 0.90 | 0.81 | 0.75 | 0.68 | 0.48 |
| 5 | 0.87 | 0.76 | 0.69 | 0.57 | 0.39 |
| 10 | 0.85 | 0.72 | 0.63 | 0.56 | 0.39 |

From the Equation (4), known the empirical coefficient α and upon obtaining the mean concentration and wind speed values, it is possible to quantify, with errors below 10%, the flow of the fugitive gas of interest (for example, methane) emitted by the generic dispersed source, whether uniform or non-uniform.

The flow calculation with Equation (4) does not require the knowledge of the source position, but only the experimental values of mean concentration $\bar{c}_H$ and the values of mean speed of the wind $\bar{u}$, according to what described above. The position of the source is located in an independent manner from the flow calculation, as described below. In this sense the proposed method is different from the models used in U.S. Pat. No. 6,895,335 and in WO 2009/156437 A2, where the determination of the flow and of the source position may not be uncoupled and requires therefore more onerous calculation procedures and a much higher number of data than that in the proposed method.

Figure 3:
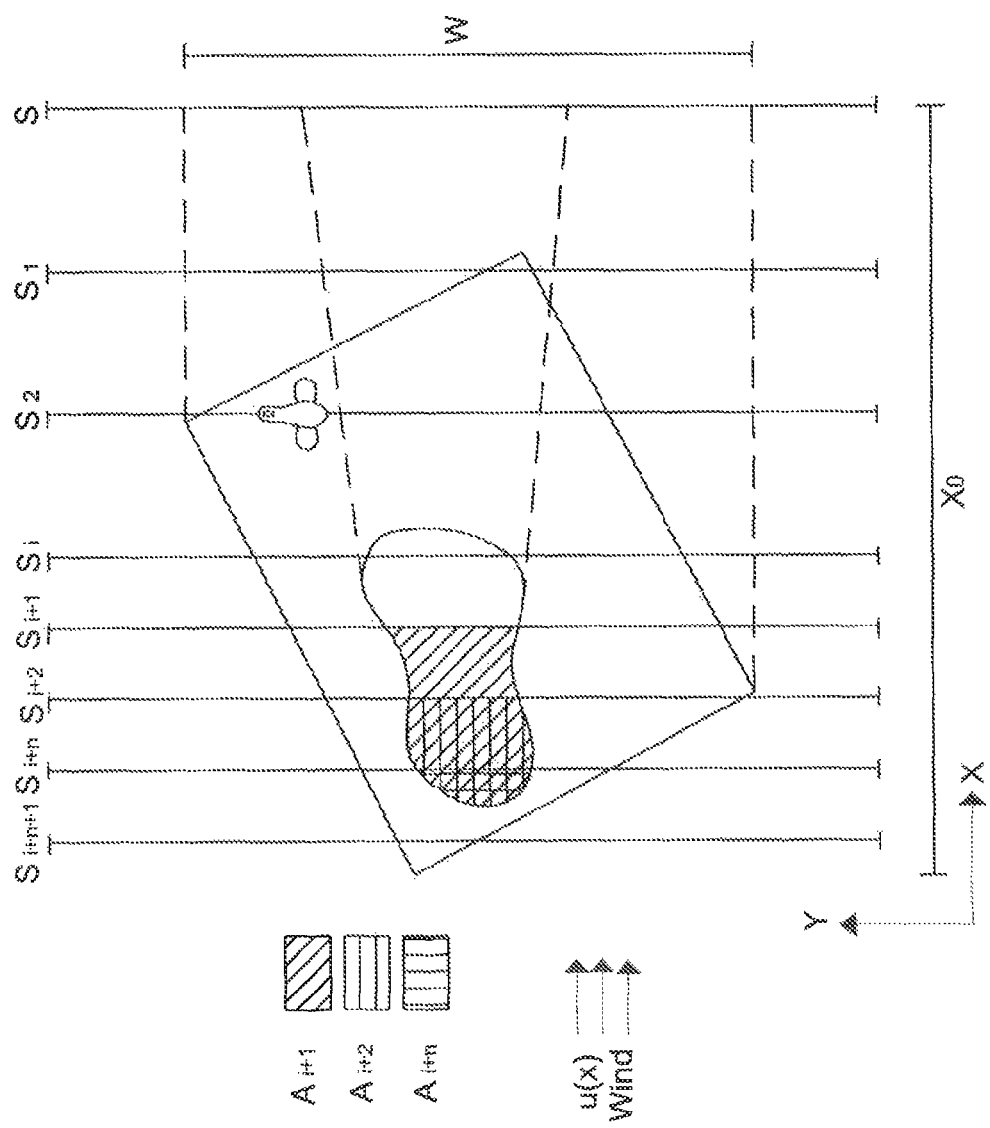
FIG. 3 represents a top view of the site to be monitored in which there are outlined planes parallel to the sampling plane of the source of emission of the fugitive gas.

Once the flow is known, additional information on the width of the dispersed source can be obtained from the mapping of the site through vertical concentration measurements detected along sampling planes $S_1 \ldots, S_i \ldots, S_{i+n+1}$ parallel to the sampling plane S, in the direction opposite to that of the wind and intersecting the surface P of the site to be monitored, as shown in FIG. 3.

Assuming that the speed of the wind u(x,y,z) and the point flow of fugitive gas q(x,y) remain constant during the mapping of the site, the detections of concentrations along the planes $S, S_1 \ldots, S_i$, where $S_i$ is the sampling plane closest to the surface A of the dispersed source not intersecting the same, lead to the same values of total fugitive gas flow.

Otherwise for the generic mapping plane $S_{i+1}$ of the concentrations intersecting the emitting source A dividing it into two sub-areas one of which, $A_{i+1}$, remains comprised between the wind direction (at x=0) and the generic plane $S_{i+1}$. The fugitive gas flow calculated on such plane according to the Equation (4) only takes into account the flow emitted in the sub-area $A_{i+1}$. Analogously, the fugitive gas flow calculated on the planes $S_{i+2}, \ldots, S_{i+n}$, according to the Equation (4) takes into account the contribution of the flow emitted by each of the corresponding sub-areas $A_{i+2}, \ldots, A_{i+n}$, decreasing progressively. The fugitive gas flow calculated at the surface $S_{i+n+1}$, upwind with respect to the source of emission, is null.

From a comparison of the fugitive gas flow resulting between two adjacent mapping surfaces, for example $S_{i+1}$ and $S_{i+2}$, information may be obtained regarding the flow of fugitive gas regarding the part $(A_{i+2}-A_{i+1})$ of the source of emission.

The mapping, according to the outlined method, through discrete measurements, provides indications, both in the direction x and in the direction y, regarding the width of the area of dispersion and contribution in terms of flow which is designated for each sub-area in which the source of flow remains divided in direction x by the parallel surfaces $S_{i+1}, \ldots, S_{i+n}$ of acquisition of vertical concentration measurements.

The method for the quantification of the fugitive gas flow from a dispersed source according to the present invention may be subjected to variants and/or modifications without departing from the scope of protection of the invention itself as defined in the attached claims.

The invention claimed is:

1. A method for the quantification of the flow from the soil of a fugitive gas from a dispersed source (A) of said gas, comprising the following steps:
    providing an aircraft (UAV) equipped with a remote detection optical instrument;
    defining a downwind sampling plane (S) perpendicular to the wind direction, having a width (W) sufficient to contain the projection of the site to be monitored and placed at such a distance from the site as to contain, at the aircraft sampling height, the whole gaseous effluent released by the site; said method being characterized in that it further comprises the steps of
    flying over said sampling plane (S) for the whole width (W) at a height (H) with said aircraft (UAV) so that said whole fugitive gas remains below said height,
    carrying out discrete vertical measurements of fugitive gas concentration averaged over said height along the whole width (W) of said plane (S) to yield corresponding mean vertical concentration values,
    detecting mean wind speed values at said discrete vertical measurements of concentration;
    integrating the product of said mean vertical concentration values and said corresponding mean wind speed values with respect to the surface of the sampling plane (S) to obtain a value of the fugitive gas flow (Q); and
    correcting the obtained value of the fugitive gas flow (Q) by a corrective factor (α) dependent from the vertical gradient of speed and concentration and obtainable by comparing concentration values obtained by direct measurements and values calculated by dispersion models in order to take into account the speed variation with the height thereby improving the accuracy of the obtained value of the fugitive gas flow (Q) from the dispersed source (A).

2. The method according to claim 1, wherein said remote detection optical instrument is a spectroscopic absorption diode laser (TDLAS).

3. The method according to claim 1, wherein said aircraft (UAV) is an autopilot aircraft.

4. The method according to claim 1, wherein the mean wind speed values are obtained from diagnostic meteorological models that process data from meteorological stations placed in strategic points of the field to be monitored.

5. The method according to claim 1, wherein the dispersion models for calculating said correction coefficient (α) are Gaussian dispersion models or commercially available dispersion models (CALPUFF).

6. The method according to claim 1, further comprising:

carrying out vertical concentration measurements along sampling planes $S_1, \ldots, S_i, \ldots, S_{i+n+1}$ parallel to said sampling plane (S), in the direction opposite to that of the wind and also intersecting the surface of said dispersed source (A), in the planes $S_1, \ldots, S_i$ not intersecting said surface, the value of the flow being constant, defining the sampling planes $S_{i+1}, \ldots, S_{i+n+1}$ intersecting the surface of said dispersed source (A) at which the value of the total fugitive gas flow decreases until zero, and obtaining the coordinates of said planes to localize said dispersed source.

* * * * *